United States Patent [19]

Phelps, Sr.

[11] 4,411,272
[45] Oct. 25, 1983

[54] MINIATURE, BATTERY-POWERED CATHODE RAY TUBE DISPLAY HEART MONITOR

[76] Inventor: Jerry A. Phelps, Sr., 6013 Innes Trace Rd., Louisville, Ky. 40222

[21] Appl. No.: 300,610

[22] Filed: Sep. 9, 1981

[51] Int. Cl.³ .............................................. A61B 5/04
[52] U.S. Cl. ................................................. 128/711
[58] Field of Search ............... 128/696, 701, 706, 708, 128/710, 712

[56] References Cited

U.S. PATENT DOCUMENTS

| | | | |
|---|---|---|---|
| 3,316,897 | 5/1967 | Weidinger et al. | 128/701 |
| 3,561,428 | 2/1971 | Jacobson | 128/712 |
| 3,590,811 | 7/1971 | Harris | 128/708 |
| 3,858,576 | 1/1975 | Dehnert et al. | 128/712 |

*Primary Examiner*—William E. Kamm
*Attorney, Agent, or Firm*—Larson and Taylor

[57] ABSTRACT

A lightweight, small size, battery-powered cardioscope is provided which can be readily transported along with a patient whose heart is being monitored and conveniently mounted directly adjacent to the operating field. The cardioscope detects heart activity using conventional electrodes and includes an audio signal device for producing an audible beep for each heart-beat and a cathode ray tube display for displaying the detected cardiac electrical activity.

1 Claim, 2 Drawing Figures

MINIATURE, BATTERY-POWERED CATHODE RAY TUBE DISPLAY HEART MONITOR

FIELD OF THE INVENTION

The present invention relates to devices and systems for detecting the electrical activity of the heart and displaying information relating to that activity.

BACKGROUND OF THE INVENTION

In U.S. Pat. No. 3,646,931 (Phelps et al.) there is described a "portable battery-powered instrument for visualizing the peripheral pulse waveform and pulse rate", which instrument possesses many advantages over prior devices designed to perform the same or similar functions. For example, a very important advantage of the instrument described in this patent is the relatively small size thereof which enables the instrument to be used with neonates (newborns). Further improvements on prior art devices in this general field are disclosed in U.S. Pat. No. 3,734,086 (Phelps, Sr.) which relates to "equipment for measuring and displaying the time lapse between a given heartbeat and the corresponding arterial pulse". These patents both disclose work of the inventor in the present application and the disclosures of both patents are hereby incorporated by reference.

The present invention represents a substantial improvement over the devices referred to above as well as other prior art heart monitoring devices and rather than discuss the problems and shortcomings of the prior art in more detail, the advantages of the present invention will be considered in relation to the prior art in general and U.S. Pat. Nos. 3,646,931 and 3,734,086, in particular, although reference may be made to these latter patents for a further discussion of the general background of this invention and the prior art.

SUMMARY OF THE INVENTION

In accordance with the invention, a self-contained, portable cardioscope or heart monitor apparatus is provided which is of very small size and light weight as compared with conventional prior art electrocardiograph devices and which thereby provides a number of advantages not available with such prior art devices. For example, the cardioscope of the invention may be mounted on an operating table in direct view of the anesthesiologist, i.e., between the anesthesiologist and the operating field. Moreover, the cardioscope may be conveniently mounted on any suitable support such as an I.V. pole or the like. Further, the unit may be transported while directly attached to, or located immediately adjacent to, the patient and, being truly portable, may be carried in a pocket or a medical bag. In this regard, a prototype of the cardioscope of the invention is 2 inches high by 3½ inches wide by 6 inches deep and has a weight of approximately one pound, although it will be appreciated that these dimensions and weight are merely exemplary and that a device with a weight and dimensions even approaching these would be highly advantageous.

The cardioscope of the invention also provides other advantages. For example, the device is battery-powered and, in an exemplary embodiment, produces a continuous nine hour display on a cathode ray tube. The batteries are rechargeable and are rechargeable, through a jack on the monitor provided with a separate transformer. An audible "beep" is provided for each heartbeat and auxiliary devices such as an hours of use indicator are readily adapted thereto. The volume of the beep produced as well as the horizontal sweep speed and vertical deflection sensitivity of the cathode ray tube may be readily adjusted by the user.

The cardioscope of the invention also possesses many specific advantages over the devices disclosed in U.S. Pat. Nos. 3,646,931 and 3,734,086. These advantages include the extremely low power requirements which result from the simplified circuitry and high resistance circuits employed by the cardioscope or heart monitor of the invention. However, these and other advantages can best be understood and appreciated from the detailed description of a preferred embodiment of the invention found hereinbelow.

DETAILED DESCRIPTION OF A PREFERRED EMBODIMENT

Figure 1:
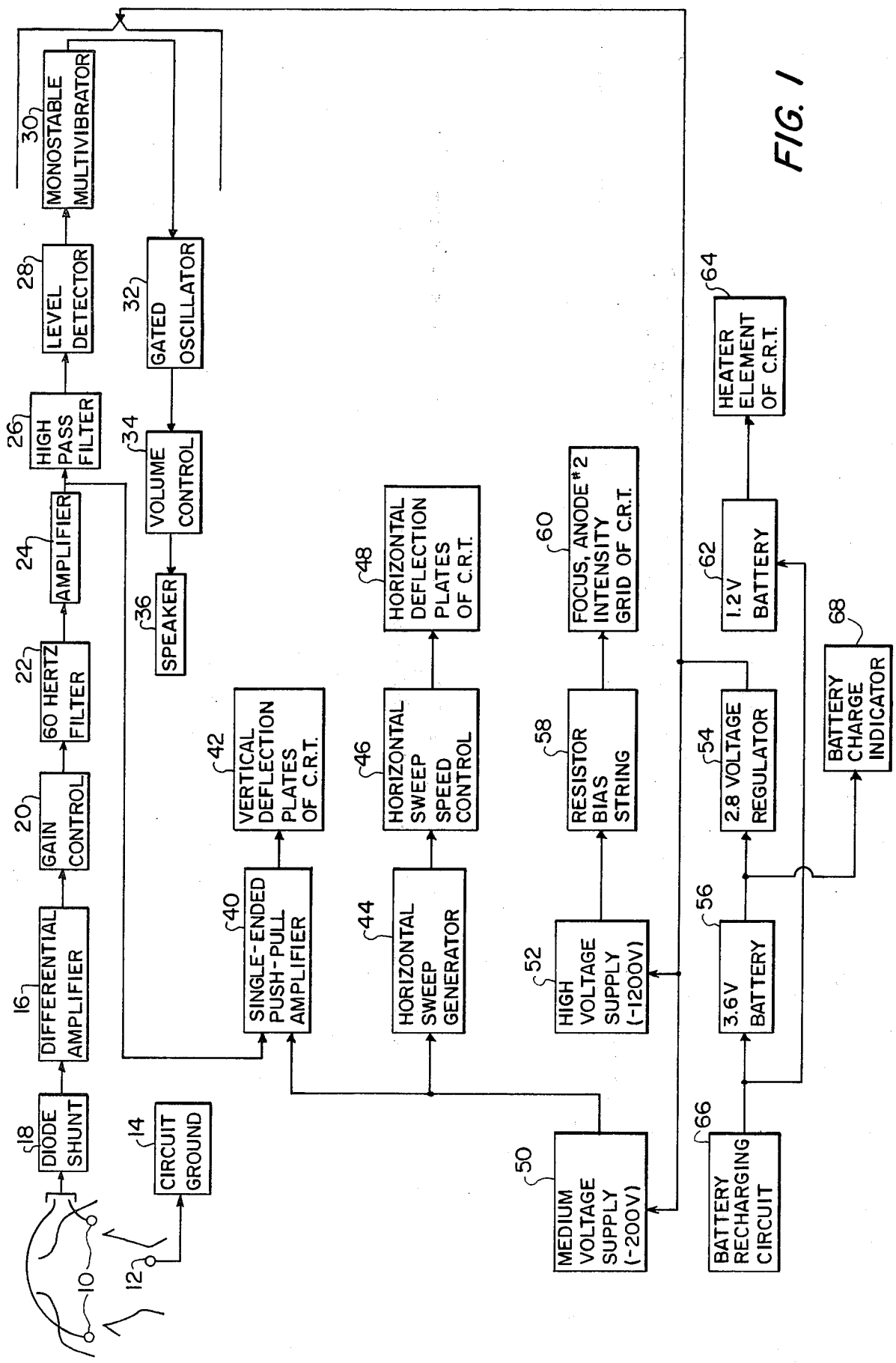
FIG. 1 is a block circuit diagram of the basic components of the cardioscope of the invention.

Referring to FIG. 1, a block diagram of the cardioscope of the invention is shown. The cardioscope of the invention can be connected to a patient using standard electrodes and direct wiring to the unit. In the exemplary embodiment shown in FIG. 1, a pair of standard silver-silver chloride electrodes 10 filled with a conventional conductive paste are connected to two separate points on the body of a patient P distant from the heart so as to detect the electrical activity of the heart. A third silver-silver chloride electrode 12, also filled with a conventional conductive paste, is used to ground the patient P to the system ground circuit, represented schematically by block 14. Electrode 12 may be, in general, placed anywhere on the skin of patient P. The electrodes 10 and 12 are small enough to enable them to be used with newborns as well as adults and these electrodes may be attached to the patient using any suitable means such as adhesive tape.

The electrical output corresponding to the electrical activity sensed by electrodes 10 is amplified by a differential input amplifier 16. Differential amplifier 16 provides improved common mode rejection over conventional input amplifiers used in the prior art and a diode shunt 18 protects amplifier 16 against circuit overloads.

A gain control circuit 20 is connected to the output of amplifier 16. The gain control circuit 20 is continuously variable, rather than stepwise variable as in prior designs, to provide a more precise adjustment of the required amplification.

Figure 2:
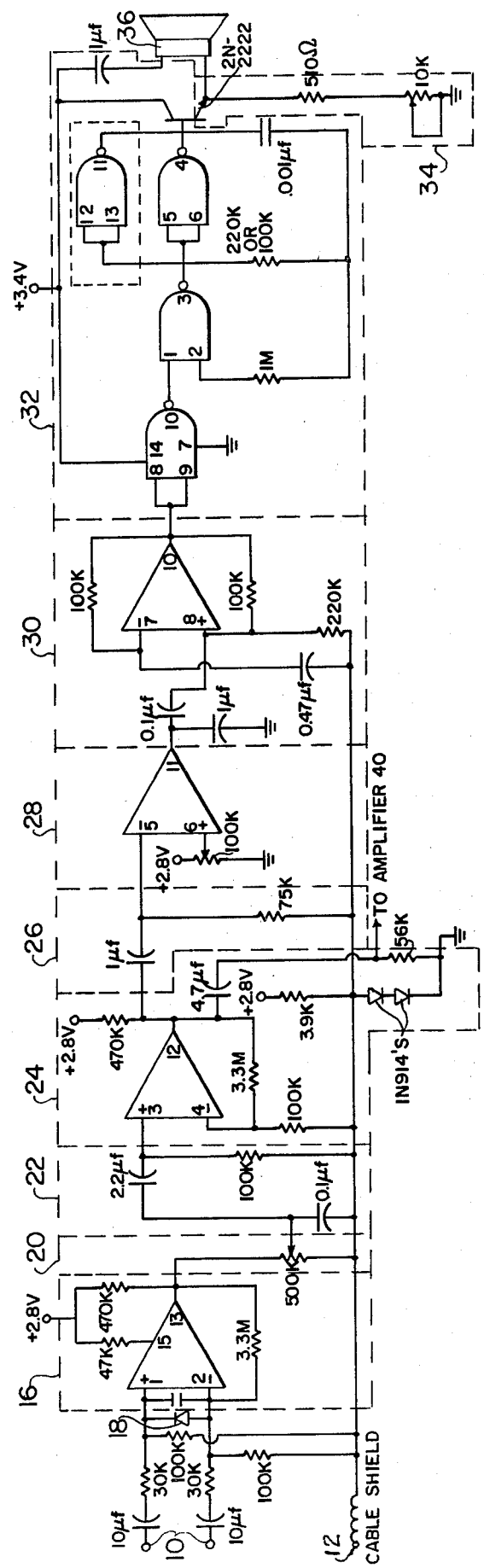
FIG. 2 is a schematic circuit diagram of a portion of the circuitry shown in block form in FIG. 2, and including exemplary component values and component identification.

A passive 60 Hertz filter 22 is connected to the output of gain control circuit 20 and serves to remove any 60 Hertz interference. The simplified passive filter circuit, which is shown in more detail in FIG. 2, includes fewer components and provides lower current drain than the filters used in the systems of my previous patents. Moreover, the 23 kiloHertz filter that was used in the previous systems has been eliminated.

An amplifier 24 is connected to the output of filter 22. In contrast to earlier designs, the gain control circuit 20 and filter 22 are separated from amplifier 22.

The output of amplifier 24 is connected to a high pass filter 26 and to a single-ended push-pull amplifier described below, the filter 26 and the amplifier in question being connected in different circuit branches or paths. The branch containing filter 28 is used in producing an audio output (the "beep" referred to above) directly related to the heartbeat and, as mentioned, may also include additional output devices such as rate meters and the like. The second branch provides the vertical deflection drive for a cathode ray tube (CRT) as described below.

Considering now the branch containing filter 28, this filter is used to pass the QRS component of the input signal, which component represents the cardiac ventricular contraction (systole).

The output of filter 26 is connected to a level detector 28 which acts as an adjustable threshold detector for a monostable multivibrator 30 connected in series therewith. This enables the adjustment for the audio output circuit described below or any additional circuits, e.g., rate meters or the like, connected in this branch, so that the QRS waveform of the electrocardiogram complex waveform will trigger multivibrator 30, but so that background noise, e.g., 60 Hertz signals or electromyographic noise, will not. It is noted that the differentiator used in previous systems has been eliminated, resulting in a simpler circuit design.

The output of multivibrator 30 is connected through a gated oscillator circuit 32 and to a volume control circuit 34 to an audio speaker 36. This circuitry is markedly simplified as compared with that of the audio signal generator used in U.S. Pat. No. 3,646,931. In this regard, reference is made to FIG. 2 which is a schematic circuit diagram of the components 10 to 34 described above, illustrating a preferred embodiment of the circuits for each block and setting forth component valves or identification for each component used. While the circuits shown in FIG. 2 will not be specifically described, it will be seen that gated oscillator 32 is formed by a single quad Nand gate integrated circuit (I.C.) connected as shown, with the Nand gate shown within the dotted lines being an extra component. It is also noted that multivibrator 30 is a fixed width monostable multivibrator which drives gated oscillator 32, in contrast to the variable width level detector used in the system disclosed in U.S. Pat. No. 3,646,931.

Referring again to FIG. 1, as mentioned above, the output of amplifier 26 is also connected to a single-ended, push-pull amplifier, which is denoted 30 in FIG. 1. Amplifier 40 provides markedly increased resistance and decreased loading as compared with the differential amplifier used in the system of U.S. Pat. No. 3,646,931. Amplifier 40 drives, in a push-pull manner, the vertical deflection plates, denoted 42, of the CRT referred to above. The cathode ray tube is used to display the pulse-like waveform produced by the heart as picked up by electrodes 10 and may advantageously comprise a Sylvania 3BGP7 cathode ray tube having a very small (1¼ inch by 3 inch) screen. Gain control circuit 20 may be adjusted to enable relative changes in pulse amplitude to be readily measured following the administration of an anesthetic or drug, or after an operative maneuver.

A horizontal sweep generator 44, which provides a saw tooth waveform, is connected through a horizontal sweep speed control circuit 46 to the horizontal deflection plates 48 of the CRT. Circuit 46 enables the user himself to adjust the saw tooth ramp voltage.

A medium voltage supply 50, which is connected to sweep generator 44 and amplifier 40, utilizes a push-pull driver for a toroid step-up transformer (not shown), with a voltage quadrupler (not shown) providing the final voltage amplification. This results in higher conversion efficiency and less current drain as compared with previous systems. Supply 50 produces −200 v for the horizontal and vertical deflection circuits of the CRT.

A high voltage supply 52 produces −1200 v and is connected through a 2.8 volt voltage regulator 54 to a 3.6 volt battery 56. Supply 52 provides the accelerating beam voltage for the CRT and through resistor string 58, supplies intermediate voltages for the focus, anode No. 2, grid and intensity inputs of the cathode ray tube, represented collectively by block 60. A 1.2 voltage battery 62 directly powers the heater element 64 of the CRT. It is noted that the improvements discussed above enable a resistor string 58 to be employed which decreases the load on the high voltage supply 52. The circuitry used operates from a single positive supply and enables the elimination of the need for both a positive supply and negative supply such as required in the systems disclosed in U.S. Pat. Nos. 3,646,931 and 3,734,086. Voltage regulator 54 ensures that stable signals and voltages are provided throughout the system, and, for example, eliminates shifting of the horizontal or vertical traces on the CRT and changes in beam intensity on the face of the CRT.

A battery recharging circuit 66 is connected to batteries 56 and 62 and permits recharging of both batteries using an A.C. voltage supplied over a two conductor cable, as opposed to using multiple D.C. voltages over a multi-conductor cable. A battery charge indicator 68 is provided to indicate the charge on the 3.6 voltage battery 56.

Although the invention has been described in relation to an exemplary embodiment thereof, it will be understood by those skilled in the art that variations and modifications can be effected in this exemplary embodiment without departing from the scope and spirit of the invention.

I claim:

1. An cardioscope apparatus for detecting the electrical heart activity of a patient and for producing output in accordance therewith for presentation both by an associated cathode ray tube and an associated audio output device, said apparatus comprising:

electrode means, adapted to be connected to the body of a patient, for detecting the electrical activity of the patient's heart;

a differential amplifier connected to said electrode means;

a diode shunt connected across the input of said differential amplifier to protect the differential amplifier from circuit overloads;

a passive 60 Hertz filter for filtering the output of said differential amplifier;

a further amplifier for amplifying the output of said filter;

a gain control circuit separate from said further amplifier for enabling continuous adjustment of the gain of the output of said differential amplifier;

a passive high pass filter connected to the output of said further amplifier;

a monostable multivibrator for receiving as an input thereto the output of said high pass filter;

a level detector for adjusting the input to said monostable multivibrator;

a gated oscillator, including a plurality of Nand gates, connected to the output of said monostable multivibrator;

an audio output device connected to the output of said oscillator;

a volume control circuit for adjusting the volume of the output signal produced by said audio output device;

a single ended push-pull amplifier connected to the output of said further amplifier for supplying a control voltage to the vertical deflection plates of the said associated cathode ray tube, and power supply means, comprising only positive voltage batteries, for supplying the necessary supply voltages for the said associated cathode ray tube and the remainder of the circuitry for the apparatus, said power supply means including a voltage regulator for regulating the voltages supplied, said apparatus further comprising a horizontal sweep generator connected to said power supply means and the horizontal deflection plates of the cathode ray tube and, including means for adjusting the horizontal sweep speed.

* * * * *